(12) United States Patent
Ashman

(10) Patent No.: US 7,004,977 B2
(45) Date of Patent: Feb. 28, 2006

(54) SOFT TISSUE SUBSTITUTE AND METHOD OF SOFT TISSUE REFORMATION

(75) Inventor: Arthur Ashman, New York, NY (US)

(73) Assignee: A Enterprises, Inc., Westport, CT (US)

( * ) Notice: Subject to any disclaimer, the term of this patent is extended or adjusted under 35 U.S.C. 154(b) by 256 days.

(21) Appl. No.: 09/448,692

(22) Filed: Nov. 24, 1999

(65) Prior Publication Data

US 2003/0149490 A1 Aug. 7, 2003

(51) Int. Cl.
A61F 2/02 (2006.01)

(52) U.S. Cl. .............................. 623/23.73; 623/16.11; 623/11.11

(58) Field of Classification Search ............. 623/23.73, 623/23.58, 23.59; 523/113, 115; 427/2.24, 427/2.27
See application file for complete search history.

(56) References Cited

U.S. PATENT DOCUMENTS

| | | | |
|---|---|---|---|
| 4,051,598 A | | 10/1977 | Sneer |
| 4,375,968 A | * | 3/1983 | Manhart ................ 433/217 |
| 4,535,485 A | | 8/1985 | Ashman et al. |
| 4,547,327 A | | 10/1985 | Bruins et al. |
| 4,547,390 A | | 10/1985 | Ashman et al. |
| 4,728,570 A | | 3/1988 | Ashman et al. |
| 4,803,075 A | * | 2/1989 | Wallace et al. ........... 424/423 |
| 4,902,511 A | | 2/1990 | Kronman |
| 4,912,141 A | | 3/1990 | Kronman |
| 4,969,906 A | | 11/1990 | Kronman |
| 5,204,382 A | | 4/1993 | Wallace et al. |
| 5,258,028 A | | 11/1993 | Ersek et al. |
| 5,352,715 A | | 10/1994 | Wallace et al. |
| 5,356,629 A | | 10/1994 | Sander et al. |
| 5,366,756 A | * | 11/1994 | Chesterfield et al. ...... 427/2.26 |
| 5,922,025 A | | 7/1999 | Hubbard |
| 5,968,999 A | * | 10/1999 | Ramp et al. ................ 523/116 |

OTHER PUBLICATIONS

James F. Glenn, Urologic Surgery, 1991, 794,804.

* cited by examiner

Primary Examiner—David J. Isabella
(74) Attorney, Agent, or Firm—Darby & Darby

(57) ABSTRACT

A soft tissue implant material is formed from biologically-compatible polymeric particles. The particles may have a diameter of up to about 500 microns and intraparticulate pores sized for ingrowth of soft tissue. The particles may have an inner core of a first biologically-compatible polymeric material and an outer layer generally surrounding the inner core, with the outer layer comprised of a second biologically-compatible polymeric material being hydrophilic and having a composition different from the composition of the first polymeric material. The material may be utilized with collagen or other matrix materials. This material may be used in a method of reforming soft tissues by implanting the material within soft body tissues to modify soft tissue defects such as wrinkles or oral gingival tissue defects and reshape soft tissue, e.g., for urinary bladder inconvenience.

39 Claims, 2 Drawing Sheets

SOFT TISSUE SUBSTITUTE AND METHOD OF SOFT TISSUE REFORMATION

BACKGROUND OF THE INVENTION

1. Field of the Invention

The present invention relates to reformation of soft tissues within the body. More particularly, the invention relates to compositions useful in reforming the shape of soft tissues and methods of using such compositions in reforming soft tissues.

2. Description of Related Art

The medical community for many years has been attempting to develop materials and techniques to replace tissues with the body. It may be desirable to replace such tissue due to, for example, injury, disease, side effects of medical procedures and surgeries, and the aging process, for example. In addition, some patients may desire to alter their appearance for cosmetic reasons, particularly the contour of visible soft tissues. Much attention has been given to the reformation of soft tissue to locally increase its volume and change its shape.

To this end, numerous replacement materials have been tried, with certain advantages and disadvantages. Silicone has been used for decades, but can displace and harden over time. Plastic and metal implants have also been used. However, implants such as these may not have a "natural" look or feel, especially as the body changes over time.

Since the early 1980's, injectable collagen has been extensively used in various procedures. Injectable collagen is either synthetic or natural, which is derived from reconstituted bovine collagen. Injectable collagen has been used throughout the body tissues. It may be accurately controlled in both placement and amount, and may have a more "natural" look and feel than other tissue substitutes.

The primary drawback of injectable collagen is its resorbable nature. Collagen quickly undergoes proteolytic degradation within the body, resulting in relatively short clinical effectiveness. Patients must receive additional injections to maintain tissue reformation, usually at an interval of about every few months. Continual submission to the injection procedure causes the patient inconvenience, expense, and perhaps pain, discomfort, and other side effects. As with any invasive medical procedure, injection carries with it the risk of cross-contamination and infection. Moreover, as the collagen is resorbed by the body, the patient may suffer a return of the physical dysfunction the injection corrected, or experience undesirable and irregular changes in cosmetic appearance.

More recently, concern has arisen in the medical and veterinary communities regarding the transmission of tissue-born diseases among animal species and humans. For example, bovine spongiform encephalopathy may move from animals to humans and cause new variant Creutzfeld-Jacob disease, which is fatal. Accordingly, some medical experts have searched for synthetic alternatives that reduce the use of animal-based tissues.

U.S. Pat. No. 4,536,158 issued to Bruins and Ashman discloses a synthetic porous implantable bony tissue replacement. A prosthesis is formed by bonding together a material composed of polymeric particles.

U.S. Pat. Nos. 4,535,485 and 4,547,390, issued to Ashman et al., disclose a synthetic material and method for making hard tissue replacement prostheses. That material is comprised of polymeric particles coated with a hydrophilic polymeric material. The particles are of sufficient size to be packed into hard tissue areas of the body, and have pores between the particles of sufficient size for tissue, i.e., hard tissue, to grow into the pores and secure the prostheses.

U.S. Pat. No. 4,728,570 issued to Ashman et al. also discloses a hard tissue prosthesis material. That material comprises polymeric particles coated with a hydrophilic polymeric material, with calcium hydroxide distributed on the surfaces and within the material to induce hard tissue growth into the pores between the particles. The particles may be bonded together to form an implantable prosthesis or may be used as a packing material for forming a hard tissue prosthesis in vivo. The material is sold by Bioplant, Inc. of South Norwalk, Conn., under the trade name Bioplant® HTR®.

In U.S. Pat. Nos. 4,902,511 and 4,912,141 issued to Kronman, an implant for fibrous or cartilaginous tissue is disclosed. A sponge-like implant is formed by polymerizing a hydrophilic polymeric material. The implant is shaped by either polymerizing it in a mold or shaping it by cutting or grinding.

While several tissue substitute materials for bony, cartilaginous, and fibrous tissues exist, it would be desirable to have substitute materials for soft tissues. It would also be desirable to have a soft tissue replacement material that was non-resorbable, supple, flexible, and durable so that a patient would not have to undergo repeated procedures. Also, a replacement material that could be implanted in loose (particulate) form for in vivo integration that did not migrate would be highly desirable.

SUMMARY OF THE INVENTION

It is an object of the present invention to provide a soft tissue substitute.

It is another object of the invention to provide a soft tissue substitute that is at least partially non-resorbable, supple, flexible and durable so that patients do not need to undergo repeated procedures.

Another object of the invention is to minimize patient discomfort, risk of infection and side effects of repeated medical procedures.

It is another object of this invention to provide a soft tissue substitute that may be implanted into the body in loose (particulate) form, that does not migrate.

It is a further object of this invention to provide a soft tissue substitute that is synthetic, bioinert and may contain natural materials.

It is yet another object of the invention to provide a soft tissue substitute that may be used to reform and augment soft tissues, including soft tissue contour defects.

The present invention is a soft tissue implant material comprising biologically-compatible polymeric particles. The particles may have a porous surface. The particulate nature of the material provides a natural feel and is held by the body's existing tissue and tissue formed into the pores and around and between the particles. The implant material may be combined with a variety of matrix materials, including collagen. The volumetric ratio of particles to matrix material may be varied depending on the application, i.e. the soft tissue intended to be replaced. The particles may compose up to 100% of the volume of the material. The implant material may also contain bioactive substances, which may, for example, be grafted to the particles. The implant material may be formed by known methods.

The invention also features methods for reforming and augmenting soft tissues. The implant material may be implanted into soft tissue at a desired location. In injectable form it may be accurately placed within soft tissue using a syringe or orthoscopic device. In this manner, the implant material may be used to correct soft tissue defects, (e.g. by plumping and expanding tissues) remediate medical conditions such as incontinence, and for cosmetic procedures.

BRIEF DESCRIPTION OF THE DRAWINGS

The foregoing and other features of the present invention will be more readily apparent from the following detailed description and drawings of an illustrative embodiment of the invention where like reference numbers refer to similar elements throughout the several view and in which.

DESCRIPTION OF THE PREFERRED EMBODIMENTS

Figure 1:
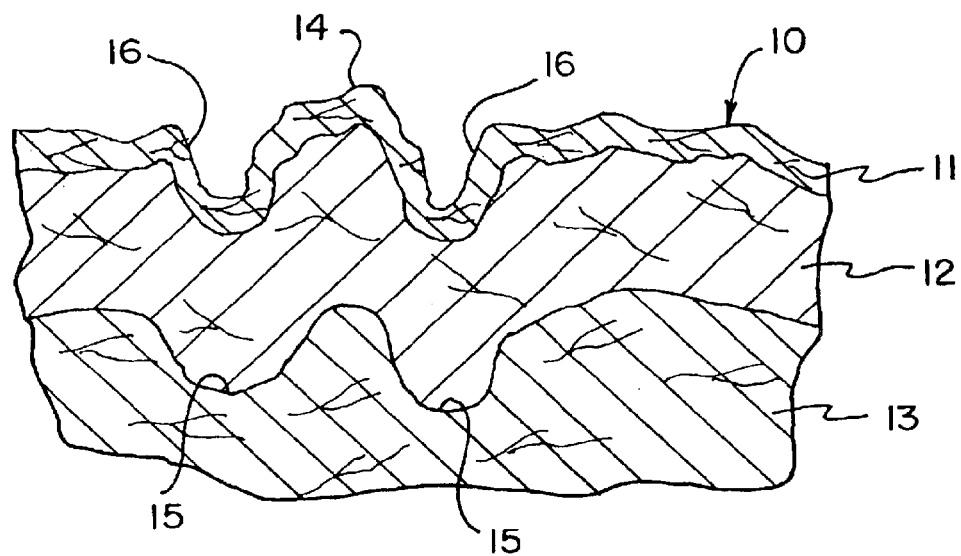
FIG. 1 shows a cross-sectional schematic of cutaneous soft tissue having a contour defect.

The present invention features materials that may be implanted into soft body tissue for correction of soft tissue defects or for soft tissue augmentation. The material comprises biologically-compatible polymeric particles, which have intraparticulate pores. The material may be combined with collagen or other matrix materials including, but not limited to, blood, saline, sterile water or glucose. The matrix material acts as a medium for particles and may help in the dispensing, e.g., injection, of the material when first implanted. The use of matrix materials also allows the amount of soft tissue augmentation to be more accurately controlled. As matrix material is resorbed, additional implantation can be accomplished, as necessary. The volume of matrix material in the implant material is preferably between about 30% and 65%. Most preferably, the volume of is about 50%. However, one skilled in the art will appreciate how much matrix material to combine to obtain a particular desired result.

A combination of the particulate material and collagen has several advantages. First, collagen has a known consistency. Second, collagen is resorbable by the body, and is completely resorbed over a period of a few months. Synthetic particles are not resorbed, and may be permanently retained bioinertly within the tissue. Collagen has a natural look and feel when injected for cosmetic applications, helping ensure the patient is satisfied with the outcome. Porous synthetic particles offer a similar outcome.

In another embodiment of the invention, the implant material may be combined with adipose (fat) tissue. Fat tissue acts as a bulking agent that helps to dispense and hold the implant material in place after implantation. Fat is also resorbable by the body, and when taken from the patient's own body, the risk of rejection of is significantly reduced. As discussed herein, other embodiments of the invention may utilize matrix materials to facilitate delivery of the material to the implantation site.

In a further embodiment of the invention, the implant material may contain bioactive substances. These substances can be therapeutic and, for example, promote tissue growth, i.e., growth factors, or act as an antimicrobial. These substances may also be grafted to or absorbed by the particles, and may be of a nature so that they are time-released in the surrounding tissue. Those skilled in the art will recognize the various bioactive substances that may be incorporated into the implant material and their medical value, depending on the application.

Preferably, the polymeric particles have an hollow inner core, and an outer layer of a different, hydrophilic polymeric material such as polymeric hydroxyethylmethacrylate (PHEMA), which preferably is comprised of a copolymer of monomeric hydroxyethylmethacrylate and a cross-linking agent. Preferred cross-linking agents include triethyleneglycol dimethacrylate, tetraethyleneglycol dimethacrylate, diethyleneglycol dimethacrylate, and monoethyleneglycol dimethacrylate. Cross-linking agents preferably comprise from about 0.1 percent to about 5 percent by weight of monomeric hydroyethylmethacrylate. The inner core is preferably an acrylic polymer, such as polymethylmethacrylate (PMMA). In another embodiment of the invention, calcium hydroxide coats the outer layer. Calcium hydroxide has an alkaline effect that may reduce acidic environments that have been associated with infection. Suitable material includes various formulation of Bioplant® HTR® available from Bioplant, Inc.

When this material is implanted into soft tissue, dense, fibrous and flexible tissue forms around and into the porous portion of the material. This occurs within a few days of implantation. The implanted material remains inert within the body, and with the newly formed tissue, augments or shapes the soft tissue as desired.

The composition of the implant material determines the nature of the tissue formation. Generally, vascularization is undesirable with soft tissue augmentation. Therefore, the particles are preferably about 500 microns in diameter or less, preferably about 50 to about 200 microns. Larger particle sizes may result in interstices between particles that are large enough to allow unwanted vascularization. In addition, growth of tissue into the implant material is dependent upon the presence and size of pores in the particles. Ingrowth helps integrate and retain the implant material in place. Preferably, the proportion of pores in the material is from about 0 percent to about 60 percent, with pore sizes of less than about 100 microns. This allows sufficient retention of the material while maintaining a high proportion of augmenting particles. Most preferably, the proportion is from about 40 to about 60 percent, and pore sizes between about 50 and about 100 microns.

Preferred procedures for producing the polymeric particles for implant materials of the invention are disclosed in U.S. Pat. Nos. 4,535,485 and 4,547,390, the specifications of which are incorporated herein by reference. In various embodiments of the present invention, the particles may be of about 34 mesh size or smaller (particle diameters of about 500 microns or less). For embodiments of the invention containing calcium hydroxide, preferred procedures for producing polymeric particles are disclosed in U.S. Pat. No. 4,728,570, which is incorporated herein by reference.

Combining the particulate material with the matrix material may be accomplished by various methods, depending on the application. In applications where the implant site will be exposed, for example, the particulate material and matrix material may be combined into a paste. In embodiments where the implant material is to be injected, the particulate material may be placed in a syringe and the matrix material drawn into the syringe to "hydrate" the material. Those skilled in the art will appreciate these and other methods of preparing the implant material.

The present invention also contemplates a method of soft tissue augmentation. Soft-tissue implant materials of the invention are inexpensive to manufacture and may be used to advantage in many medical, dental, cosmetic, and veterinary applications. The material may be implanted into specific tissues in the body to provide desired augmentation. Preferably, the material is combined with one or more matrix materials before implantation. Preferred matrix materials are sterile water, saline solution, collagen, blood and glucose. In order for there to be ample fluidity, the matrix material may comprise a volume of between about 30% and about 65%, and most preferredly about 50%, of the implanted material. Those versed in the art will appreciate which and how much matrix material to use for a particular application.

In certain embodiments of the invention, the implant material is injected, e.g., by syringe or orthoscopic devices. These methods are preferred because they are less invasive than other, e.g., surgical, procedures, lessen the risk of infection, discomfort, and complications, and can be easily controlled in amount and location. For materials containing collagen, it is preferable that the collagen be in injectable form. One skilled in the art will know the various methods of injection. For example, embodiments of the invention having a particle size of about 500 microns may be injected using an 18-gauge syringe. Those embodiments having smaller particles may be injected with higher-gauge needles, e.g., orthoscopically.

In one embodiment of the invention, the implant material is injected subcutaneously into an area having a soft tissue contour defect. The amount implanted is in a sufficient amount to at least partially, preferably entirely, remove the defect. Such defect may include, for example, wrinkles.

Referring to the drawings, and initially to FIG. 1, skin 10 consists of the epidermis 11 and the dermis 12. The hypodermis 13, also called the subcutaneous layer, contains collagen, elastic tissue, and adipose (fat) (not shown in any more detail). The hypodermis 13 provides underlying structure for the skin, and thus greatly contributes locally to its contour 14. The hypodermis 13 may lose its adipose, collagen, and elastic tissue, especially as the skin 10 ages. This can result in vacuities 15 in the hypodermis and loss of support for the overlaying dermis 12 and epidermis 11, i.e., the skin sags, forming wrinkles 16.

Figure 2:
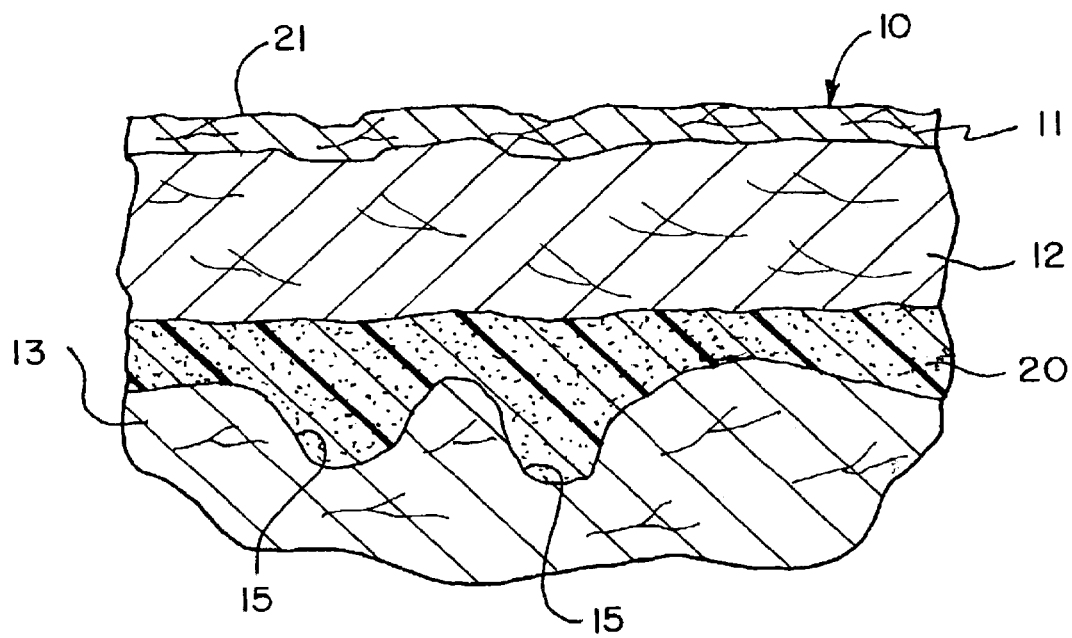
FIG. 2 shows a cross-sectional schematic of the cutaneous tissue of FIG. 1 after the implant material of the present invention has been implanted subcutaneously.

In FIG. 2, the implant material 20 of the present invention has been injected under the skin 10 into the hypodermis 13 beneath the dermis 12. The implant material 20 fills the vacuities 15, providing support for the skin 10. The material 20 also pushes out the skin 10, causing it to have a much smoother surface contour 21.

Figure 3:
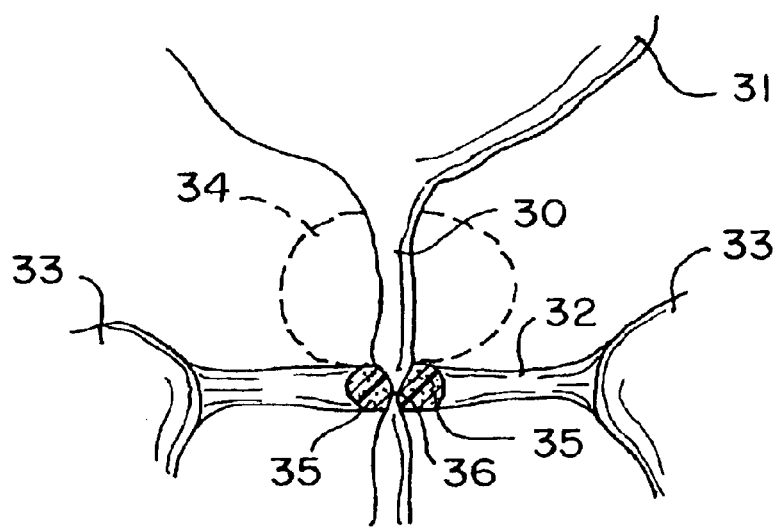
FIG. 3 shows a schematic of a portion of the human male urinary tract after prostrate removal with constriction of the urethra after the implant material of the present invention has been injected into the sphincter urethrae.

In another embodiment of the invention, the implant material may be used to control incontinence. Such incontinence may be the result of disease, aging, or neuromuscular degeneration. It may also result from prostate surgery that causes localized damage to the nerves controlling the sphincter surrounding the urethra. As shown in FIG. 3, the urethra 30 is connected to the bladder 31. The sphincter urethrae 32 is attached to the pelvis 33 and surrounds the urethra 30. The prostate 34 (shown in phantom) which surrounds the urethra 30 between the bladder 31 and the sphincter urethrae 32 is shown as having been previously removed surgically. Often this surgery damages the controlling sphincter urethrae 32 or causes indirect flaccidity due to nerve damage. Where a patient has lost some or all control of the sphincter urethrae 32, he will not be able to constrict the urethra 30 and prevent urine flow. In the present invention, implant material 35 is injected into the sphincter urethrae 32, swelling it, reshaping it, and causing at least a partial closure and constriction 36 of the urethra 30. Contraction of other muscles, e.g., the abdominal muscles, in the area of the bladder (not shown) will push the sphincter 32 and allow urine to flow past the constriction 36, even where there is no direct control over the sphincter.

Preferably, between about 2 cc and about 4 cc of implant material is injected into the sphincter urethrae 32 to cause constriction 36 of the urethra 30. However, one skilled in the art will appreciate how much implant material to inject according to the particular medical condition of the patient.

Those skilled in the art will recognize that the compositions and methods of the present invention will have various other uses in addition to the above described embodiments. They will appreciate that the foregoing specification and accompanying drawings are set forth by way of illustration and not limitation of the invention. It will further be appreciated that various modifications and changes may be made therein without departing from the spirit and scope of the present invention, which is to be limited solely by the scope of the appended claims.

What is claimed is:

1. A soft tissue implant material comprising biologically-compatible non-resorbable polymeric particles having a coating of calcium hydroxide thereon, wherein said particles have interstices therebetween having dimensions effective to permit soft tissue to grow therein.

2. The implant material of claim 1, wherein the particles have intraparticulate pores, said pores having dimensions effective to permit soft tissue to grow therein.

3. Implant material of claim 1 wherein said particles have a diameter of up to about 500 microns.

4. Implant material of claim 3 wherein said particles have a diameter of about 50 to about 200 microns.

5. Implant material of claim 2 wherein said pores comprise up to about 60 percent of said implant material.

6. Implant material of claim 5 wherein said pores comprise between about 40 and about 60 percent of said implant material.

7. Implant material of claim 2 wherein said pores have a size of less than about 100 microns.

8. Implant material of claim 7 wherein said pores have a size of between about 50 and about 100 microns.

9. Implant material of claim 1 further comprising collagen.

10. Implant material of claim 9 wherein said collagen comprises between about 30% and about 65% of said implant material by volume.

11. Implant material of claim 10 wherein said collagen comprises about 50% of said implant material by volume.

12. Implant material of claim 9 wherein said collagen comprises injectable collagen.

13. Implant material of claim 1 wherein said particles have an inner core comprised of a first biologically-compatible polymeric material and an outer layer generally surrounding said inner core, said outer layer comprised of a second biologically-compatible polymeric material, said second polymeric material being hydrophilic and having a composition different from the composition of said first polymeric material.

14. Implant material of claim 13 wherein said first polymeric material is an acrylic polymer.

15. Implant material of claim 14 wherein said first polymeric material is polymethylmethacrylate.

16. Implant material of claim 13 wherein said second polymeric material is a polymeric hydroxyethylmethacrylate.

17. Implant material of claim 16 wherein said polymeric hydroxyethylmethacrylate comprises a copolymer of monomeric hydroxyethylmethacrylate and a cross-linking agent.

18. Implant material of claim 1 further comprising at least one bioactive substance.

19. Implant material of claim 18 wherein said at least one bioactive substance is grafted to said biologically-compatible particles.

20. A particulate soft tissue implant comprising the material of claim 1.

21. A particulate soft tissue implant comprising particles having an inner core comprised of polymethylmethacrylate and an outer layer generally surrounding said inner core comprised of polymeric hydroxyethylmethacrylate, said particles having interstices therebetween with dimensions effective to permit soft tissue to grow therein.

22. The implant of claim 21, wherein said particles have intraparticulate pores with dimensions effective to permit soft tissue to grow therein.

23. Implant of claim 22 wherein said pores comprise up to about 60 percent of said implant material.

24. Implant of claim 23 wherein said pores comprise between about 40 and about 60 percent of said implant material.

25. Implant of claim 22 wherein said pores have a size of less than about 100 microns.

26. Implant of claim 25 wherein said pores have a size of between about 50 and about 100 microns.

27. Implant of claim 21 wherein said particles have a diameter of up to about 500 microns.

28. Implant of claim 27 wherein said particles have a diameter of about 50 to about 200 microns.

29. Implant of claim 21 further comprising collagen.

30. Implant of claim 29 wherein said collagen comprises between about 30% and about 65% of said implant material by volume.

31. Implant of claim 30 wherein said collagen comprises about 50% of said implant material by volume.

32. Implant of claim 29 wherein said collagen comprises injectable collagen.

33. Implant of claim 21 further comprising at least one bioactive substance.

34. Implant of claim 33 wherein said at least one bioactive substance is grafted to said biologically-compatible particles.

35. A soft tissue implant material comprising at least partially non-resorbable biologically-compatible polymeric particles having a coating of calcium hydroxide thereon, wherein said particles have interstices therebetween having dimensions effective to permit soft tissue to grow therein.

36. A particulate soft tissue implant comprising the material of claim 35.

37. A soft tissue implant material comprising at least partially non-resorbable biologically-compatible polymeric particles having an amount of calcium hydroxide thereon effective to induce soft tissue growth, wherein said particles have interstices therebetween having dimensions effective to permit soft tissue to grow therein.

38. A particulate soft tissue implant comprising the material of claim 37.

39. Implant material of claim 36, wherein the biologically-compatible polymeric particles are non-resorbable.

* * * * *